United States Patent [19]

Austin

[11] 4,274,412
[45] Jun. 23, 1981

[54] TAMPON CONTAINING BLENDED SUPERABSORBENT MATERIAL

[75] Inventor: Jared A. Austin, Appleton, Wis.

[73] Assignee: Kimberly-Clark Corporation, Neenah, Wis.

[21] Appl. No.: 87,221

[22] Filed: Oct. 22, 1979

[51] Int. Cl.³ ............................................. A61F 13/20
[52] U.S. Cl. .................................................. 128/285
[58] Field of Search ................... 128/285, 290 R, 296

[56] References Cited

U.S. PATENT DOCUMENTS

| | | |
|---|---|---|
| 1,887,526 | 11/1932 | Spielberg et al. .................. 128/285 |
| 2,643,656 | 6/1953 | Atkinson ......................... 128/290 R |
| 3,055,369 | 9/1962 | Graham, Jr. ....................... 128/285 |
| 3,294,091 | 12/1966 | Morse ............................. 128/290 R |
| 4,041,948 | 8/1977 | Flam et al. ........................ 128/285 |

FOREIGN PATENT DOCUMENTS

| | | |
|---|---|---|
| 197808 | 8/1978 | France ............................. 128/285 |
| 197808 | 8/1978 | Netherlands ..................... 128/285 |

*Primary Examiner*—C. Fred Rosenbaum
*Attorney, Agent, or Firm*—Howard Olevsky; William D. Herrick

[57] ABSTRACT

A tampon is provided having an absorbent core made of a plurality of discrete plies of a blend of cellulosic material and superabsorbent fibers and having an absorbent layer overwrap and a fluid permeable cover surrounding the absorbent material. The absorbent layer is located on both the top and bottom surfaces of the absorbent core and contains staple textile fibers.

8 Claims, 2 Drawing Figures

TAMPON CONTAINING BLENDED SUPERABSORBENT MATERIAL

FIELD OF THE INVENTION

This invention relates to a tampon and particularly to a tampon containing superabsorbent material.

BACKGROUND OF THE INVENTION

Much attention has been paid of late to the development of tampons which contain superabsorbent material. Superabsorbents are usually polymeric in nature, having a much greater capacity for fluid per unit weight than the cotton and rayon fibers commonly utilized as the absorbent media in the most popular commercial tampons now being marketed. [Examples of these materials which are commercially available are: BUCKEYE CLD which is a trademark of Procter & Gamble and consists of carboxymethylated wood pulp fibers; ABSORBIT, a trademark of American Enka, Division of Akzona Inc. which is an alloyed cellulose fiber containing an alkali metal salt of ammonium salt of a copolymer or terpolymer of acrylic acid and/or methacrylic acid and AQUALON which is a trademark of Hercules Inc. and is a material made of carboxymethylated cotton linters.] Generally these superabsorbents are added at a level of 5 to 30 percent to conventional cotton or rayon fibers. By so doing, tampons of vastly improved capacity and better efficiency per unit weight are provided. The inclusion of these superabsorbent materials allow the user to wear the tampons for an extended period of time when compared to the tampons previously available. However, one noticeable shortcoming of these higher capacity tampons not experienced with conventional tampon products is difficulty associated with withdrawal of the used tampon. Tampons containing superabsorbent have greater frictional drag than conventional tampons. This is particularly noticeable when the superabsorbent containing tampons are removed early and/or when they contain relatively small amounts of absorbed fluid where only a portion of the tampon capacity was utilized. In any event users have reported a perceivable increase in frictional drag during withdrawal.

Several attempts have been made to minimize the problems associated with withdrawal and have included, providing a softer lower density and less compressed tampon pledget, providing a narrower pledget, isolating the superabsorbent material in the tampon interior, tapering the withdrawal end of the tampon, using smoother wrapper material to reduce friction and even adding a surfactant to the wrapper to act as a lubricant in an attempt to reduce frictional drag.

In another approach, various attempts have been made to segregate the superabsorbent material from the vaginal membrane while maintaining the highly absorbent character of the superabsorbent material. These attempts have usually led to interference with fluid absorption or, failure to significantly affect the frictional drag associated with the presence of the superabsorbent within the absorbent media.

SUMMARY OF THE INVENTION

This invention provides a tampon in which significant absorptive benefit is obtained by the presence of superabsorbent without the associated difficulty in removal.

The tampons of this invention include a two component absorptive system. The first portion of the absorptive system is characterized as an absorbent core. This core includes a plurality of discrete plies of a compressed blend of a mixture of superabsorbent fibers and short natural cellulosic fibers. These compressed plies or sheets are made on a conventional papermaking machine in which the fibers are intermingled and compressed according to conventional papermaking technology. The fibers are generally compressed by a factor of approximately 50 percent and reach a thickness of about 0.05 inches after compression. Depending upon the desired overall configuration of the tampon and particularly its thickness, five to eight plies of the compressed fibrous sheets are used for the absorbent core, and the superabsorbent material is generally present in amounts varying up to 30 percent by weight of the blend in the individual sheet.

While overall compositions of absorptive blends containing both conventional cellulosic fibers such as wood pulp and cotton linters in conjunction with a superabsorbent are known, the combination of the superabsorbent core in its designated form along with the other components of this system define a unique mode for obtaining the advantages of the superabsorbent without the accompanying difficulties in removal.

In order to obtain ease in removal, superabsorbent material must be available for absorption but not be in contact with the vaginal tissues. To provide the proper environment for accomplishing these goals, another absorbent layer of material is provided to both the top and the bottom of the absorbent core. This layer, according to the invention, contains a significant amount of staple textile fibers. The textile fibers may consist of any of the conventional materials such as rayon, cotton or polyester but they must be present in a significant amount and most especially desired is an outer absorptive layer which contains substantially 100 percent of these staple textile fibers.

The difference between staple textile fibers and the fibers used to blend with the superabsorbent material is a function of fiber length. Fibers which are ½ inch or longer are denominated as staple textile fibers while shorter fibers are those which are utilized in conjunction with the superabsorbent material on papermaking apparatus. Textile fibers may be natural or synthetic and is generally in bales.

The general construction of the tampon may vary according to various design parameters but an exemplary embodiment as set forth in FIGS. 1 and 2 which embody the concept of the subject invention.

According to the FIGS.:

Figure 2:
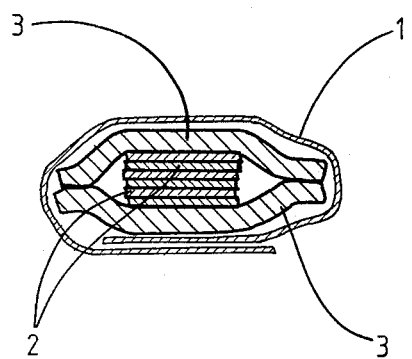
FIG. 2 is a cross section taken along lines 2—2 in FIG. 1.

As shown in the drawings, several plies of the composite absorptive sheet material 2 are located along a planar axis in the central portion of the tampon. Immediately surrounding the core is an upper and lower textile fiber absorptive layer 3. As shown in FIG. 2, in a particularly preferred embodiment, the absorptive upper and lower layer 3 extends beyond the sides of the absorptive core material and actually abut along the longitudinal axis of the absorptive core.

A withdrawal string 5 is wrapped around the entire thickness of the tampon at one end, a hole is produced central to the vertical axis and the string is passed through the hole and knotted to hold the component layers in position.

Surrounding the absorptive material is a fluid pervious outer wrapper 1. The wrapper is utilized as an additional outer layer or as a bag which completely encircles the end of the tampon forming the leading end on insertion depending upon the amount of textile fiber present in the absorptive layer 3. If there is more than 20 percent textile fiber present in the absorptive layer, it is unnecessary to form a bag with the fluid pervious material. The reason for this is that there is increasing structural integrity of the outer absorptive layer and, as a result, the tampon itself with increasing amounts of textile fiber. At the higher levels of textile fiber, the tampon retains its integrity even when highly saturated with menstrual fluid and there is, as a result, no need for the outer wrap to be in bag form. The 20 percent figure mentioned previously seems to provide a realistic cutoff for a level below which a bag is needed.

The outer wrapper is made of any conventional fluid pervious material, a variety of which is well known in the art.

Figure 1:
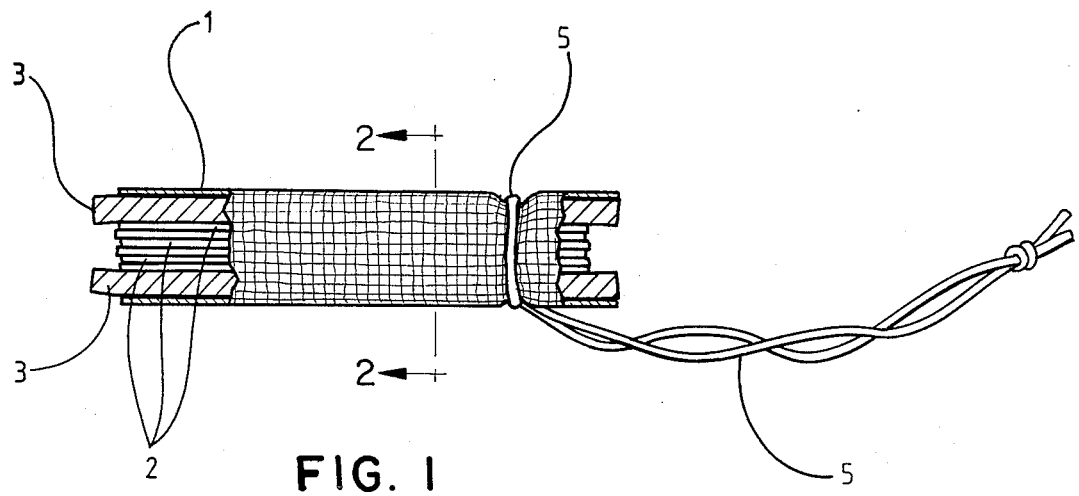
FIG. 1 is a side view partially in cross section showing the tampon of the subject invention.

The significance of the embodiments of the subject invention will be more readily understood by reference to the comparison test set forth below. A sample of the tampon described in FIGS. 1 and 2 was prepared with six plies of the superabsorbent core material and a 100 percent rayon textile fiber outer absorbent layer. The outer fluid permeable wrap was 8×5 nylon scrim with 10 gm./sq. yd. blend of 33⅓ of each of rayon, cotton and polyester. The absorbent core material contained a blend of 78 percent cotton linters and 22 percent AQUALON. After a substantial batch of these were made, they were wrapped with the cover material and compressed to fit in a conventional commercially available tampon inserter. A comparison test was undertaken between this tampon and the KOTEX H.D. super tube tampon which has an absorbent fluff blend of 20 percent AQUALON, 35 percent rayon and 45 percent cotton linters. Both the outer wrap and the tampon inserter were identical in both cases. KOTEX is a trademark of Kimberly-Clark Corporation, Neenah, Wisconsin.

An equal number of tampons were provided to a group of 86 women and these women were requested to utilize the tampons in their normal accepted pattern of use and after significant numbers of tampons of each type were used by each woman, they were asked to evaluate the tampons based on ease of insertion, ease of removal during heavy and light flow and absorption criteria. The results are set forth in the table below.

|  | Prior Art | Invention |
|---|---|---|
| All tampons - x̄ hrs. worn | 6.62 | 6.45 |
| All tampons - x̄ gms. abs. | 8.56 | 7.73 |
| Tampons with leakage - x̄ gms. absorbed | 13.56 | 12.26 |
| Tampons without leakage - x̄ gms. absorbed | 7.80 | 7.02 |
| % Leakers | 13.19 | 13.53 |
| % removal difficulty - by participants (number of panel participants experiencing difficulty) | 40.70 | 27.91 |
| % removal difficulty - by tampons (number of tampons producing removal difficulty) | 16.20 | 7.98 |

As can be seen from the data above, while there are slightly better absorptive characteristics with the heavy duty commercially available tampon there are significantly better removal characterisitics with the tampon of this invention. It is worthwhile noting that the "heavy duty" prior art tampon is designed specifically for high levels of menstrual fluid flow and that this tampon would compare favorably with the more conventional tampons designed for more normal flow.

What is claimed is:
1. A tampon comprising in combination:
   (a) an absorbent core including a plurality of discrete essentially planar, abutting plies of a compressed blend of superabsorbent fibers and short cellulosic fibers selected from the class consisting of wood pulp fibers and cotton linters;
   (b) an absorbent layer located on the bottom and the top of said core having textile length fibers;
   (c) a fluid permeable outer cover surrounding the top and sides of the absorbent surfaces; and
   (d) withdrawal means attached to one end of the tampon.
2. The tampon according to claim 1 in which the cover is a bag completely enclosing the absorbent core and absorbent layer.
3. The tampon according to claim 1 in which the absorbent layer has at least 20% textile fibers.
4. The tampon according to claim 1, 2 or 3 in which the compressed thickness of each discrete layer of the absorbent core is about 0.05 inch.
5. The tampon according to claim 1, 2 or 3 in which there are between 5 and 8 plies in the absorbent core.
6. The tampon according to claim 1, 2 or 3 in which the absorbent layer surrounds the sides of the absorbent core.
7. The tampon according to claim 1, 2 or 3 in which superabsorbent is present at an amount not greater than 30% by weight of the absorbent core plies.
8. The tampon according to claim 1, 2 or 3 in which the absorbent layer consists essentially of rayon.

* * * * *